United States Patent [19]
Hittel

[11] Patent Number: 6,136,806
[45] Date of Patent: Oct. 24, 2000

[54] REMEDY FOR ROSACEA

[75] Inventor: Norbert Hittel, Rodgau, Germany

[73] Assignee: Otsuka Pharmaceutical Co., Ltd., Tokyo, Japan

[21] Appl. No.: 09/194,058

[22] PCT Filed: May 19, 1997

[86] PCT No.: PCT/JP97/01667

§ 371 Date: Nov. 20, 1998

§ 102(e) Date: Nov. 20, 1998

[87] PCT Pub. No.: WO97/44034

PCT Pub. Date: Nov. 27, 1997

[30] Foreign Application Priority Data

May 20, 1996 [JP] Japan .................................. 8-124531

[51] Int. Cl.$^7$ ........................... A61K 31/50; A61K 31/44
[52] U.S. Cl. ........................... 514/253; 514/306; 514/859
[58] Field of Search .................................. 514/253, 859, 514/306

[56] References Cited

U.S. PATENT DOCUMENTS

| | | | |
|---|---|---|---|
| 4,399,134 | 8/1983 | Ishikawa et al. | 424/246 |
| 4,552,879 | 11/1985 | Ishikawa et al. | 514/253 |
| 5,179,096 | 1/1993 | Gentilini et al. | 514/253 |

OTHER PUBLICATIONS

Nishijima et al., Activity of Eight Fluoroquinolones Against Both Methicillin–Susceptible and –Resistant Staphylococcus, arues Isolated from Skin Infections, Journal of Dermatology vol. 22, 153–155, 1995.

Acne and Rosacea, $2^{nd}$, Completely Revised and Enlarged Edition, G. Plewig, Springer–Verlag, pp. 431, 433–455.

*Primary Examiner*—Kevin E. Weddington
*Attorney, Agent, or Firm*—Finnegan, Henderson, Farabow, Garrett & Dunner, L. L. P.

[57] ABSTRACT

A rosacea treating agent is provided, which is effective even on intractable rosacea which cannot be cured completely by antibiotics such as minocycline, has low toxicity, causes little side effect, and is of long duration. The rosacea treating agent of the present invention comprises, as an active ingredient, at least one selected from the group consisting of benzoheterocyclic derivatives represented by the following formula (1):

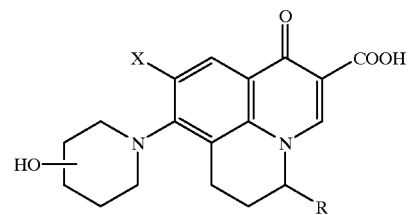

(1)

wherein R is a lower alkyl group; and X is a halogen atom, and salts thereof.

5 Claims, No Drawings

REMEDY FOR ROSACEA

TECHNICAL FIELD

The present invention relates to a treating agent for rosacea.

BACKGROUND ART

Rosacea is, while rare among colored races, common among races with a light-colored skin, especially white races, and many cases occur among them. It is divided according to the symptoms into the first degree (telangiectatic rosacea on the forehead, cheeks, dorsum nasi), the second degree (acne rosacea, coexistence of follicular papules and pustules), and the third degree (rhinophyma, dark red tumor and dilated pore on apex nasi). It starts with facial flush (redness) and eventually involves serious impairment of appearance, developing papules, pustules, rhinophyma and tumor on apex nasi, It is also accompanied by seborrhea or enhancement of feeling of heat on the face due to emotional stress or change of environmental temperature. Thus, these symptoms give a patient mental and physical suffering.

For the time being, the real cause of rosacea is unknown (*Hifuka Chirya Handbook*, pp. 380–381, Nanzando (1987) and Gerd Plewing, Albert M. Kligman, ACNE and ROSACEA, 2nd, Completely Revised and Enlarged Edition, pp. 431–454, Springer-Verlag (1993)). Rosacea is apt to be confused with acne, what is called pimple, classificationally. Rosacea, which can coexist with acne, essentially differs from acne. It is characterized by facial flush due to vascularization and proceeds with acne rosacea and tumor on apex nasi. A digestive disease, hypertension, *Demodex folliculorum*, emotional stress, hereditary predisposition, etc. have been pointed out as a conceivable cause of rosacea, which has not been ascertained yet.

Therefore, there is no drug established as a remedy for rosacea, and the only method available now is symptomatic treatment, such as administration of minocycline or tetracycline antibiotics for the treatment of delayed skin diseases, use of metronidazole (anthelmintic), removal of mental stress, dietetic treatment, and supplemental concomitant use of vitamin $B_2$ or $B_6$.

Accordingly, it has been keenly demanded to study and develop more useful treating agents for rosacea.

An object of the present invention is to provide a useful rosacea treating agent.

DISCLOSURE OF THE INVENTION

The inventor of the present invention has conducted extensive study to develop a rosacea treating agent in the light of the above circumstances, and found as a result that at least one compound selected from the group consisting of benzoheterocyclic derivatives represented by the following formula (1):

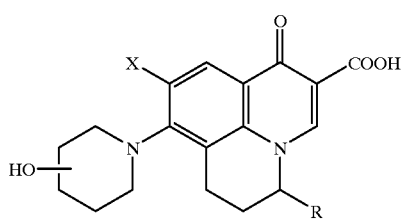

(1)

wherein R represents a lower alkyl group; and X represents a halogen atom, and salts thereof is suitable as an active ingredient of a rosacea treating agent, The present invention has been completed based on this finding.

That is, the present invention relates to a rosacea treating agent comprising at least one selected from the group consisting of the above benzoheterocyclic derivatives represented by formula (1) and salts thereof as an active ingredient; use of at least one selected from the above compounds for preparing a rosacea treating agent; and a method for treating rosacea comprising using at least one selected from the above compounds.

The benzoheterocyclic derivatives represented by formula (1) or salts thereof are known from, e.g., Japanese Patent Publication No. 41127/89, which teaches details of a method for preparing these compounds and usefulness of the compounds as antimicrobial agents.

However, it is unpredictable even for one skilled in the art whether or not these benzoheterocyclic derivatives and their salts are effective for treating rosacea that has been considered baffling and difficult to cure.

The rosacea treating agent according to the present invention is effective even for treating intractable rosacea on which conventional antibiotics such as minocycline do not work, healing rosacea active papules, active pustules, erythema, and active efflorescence, and suppressing telangiectasia. It has low toxicity, causing little side effect, and is of long duration.

BEST EMBODIMENTS FOR CARRYING OUT THE INVENTION

The rosacea treating agent according to the present invention comprises at least one selected from the group consisting of the above benzoheterocyclic derivatives represented by formula (1) and salts thereof as an active ingredient.

In formula (1), the lower alkyl group represented by R includes straight-chain or branched alkyl groups having 1 to 6 carbon atoms, such as methyl, ethyl, propyl, isopropyl, butyl, tort-butyl, pentyl and hexyl groups. The halogen atom represented by X includes a fluorine atom, a chlorine atom, a bromine atom, and an iodine atom.

Of the compounds represented by formula (1), (±)-9-fluoro-6,7-dihydro-8-(4-hydroxy-1-piperidyl)-5-methyl-1-oxo-1H, 5H-benzo[i,j]-quinolizine-2-carboxylic acid is particularly preferred.

The compound represented by formula (1) can be easily converted into acid-addition salts thereof by the reaction with a pharmaceutically acceptable acid. The acid includes inorganic acids, such as hydrochloric acid, sulfuric acid, phosphoric acid, and hydrobromic acid; and organic acids, such as oxalic acid, maleic acid, fumaric acid, malic acid, tartaric acid, citric acid, and benzoic acid. The compounds represented by formula (1) can easily be converted into salts thereof by the reaction with a pharmaceutically acceptable alkaline compound. The alkaline compound includes sodium hydroxide, calcium hydroxide, potassium hydroxide, sodium carbonate, and potassium hydrogencarbonate.

The compound represented by formula (1) of the present invention and salts thereof can be easily isolated and purified by ordinary separation means, such as solvent extraction, dilution, recrystallization, column chromatography, preparative thin layer chromatography, and the like.

In using the compound represented by formula (1) and salts thereof an a rosacea treating agent, they are generally compounded into pharmaceutical compositions together with pharmaceutically acceptable carriers which are commonly employed in preparing drugs of dose form conformable to the method of administration. Suitable carriers which can be used include diluents or excipients, such as fillers, extenders, binders, wetting agents, disintegrants, surfactants, lubricants, etc.

The rosacea treating agent can have various dosage forms in accordance with the purpose of the therapy. Typical dosage forms include tablets, pills, powders, liquid preparations, suspensions, emulsions, granules, capsules, suppositories, injectable preparations (solutions, suspensions, etc.); sprays, such as inhalations and aerosol for external use; liquids for topical application, lotions, gels, oily ointments; emulsified ointments, such as O/W hydrophilic ointments and W/O water-absorbent ointments; water-soluble ointments, creams, liniments, cataplasms, pastes, plasters, external preparation such as emulsions, and sheets.

If the pharmaceutical composition is formulated into tablets, a wide range of carriers known in the art can be used. Examples of suitable carriers include excipients such an lactose, white sugar, sodium chloride, glucose, urea, starch, calcium carbonate, kaolin, crystalline cellulose, and silicic acid; binders such as water, ethanol, propanol, simple syrup, a glucose solution, a starch solution, a gelatin solution, carboxymethyl cellulose, shellac, methyl cellulose, potassium phosphate, and polyvinylpyrrolidone; disintegrants such as dried starch, sodium alginate, agar powder, laminaria powder, sodium hydrogencarbonate, calcium carbonate, polyoxyethylene sorbitan fatty acid esters, sodium laurylsulfate, glycerol monostearate, starch, and lactose; disintegration inhibitors such an white sugar, stearin, cacao butter, and hydrogenated oils; absorption promoters such as quaternary ammonium bases and sodium laurylsulfate; humectants such as glycerol and starch; adsorbents such as starch, lactose, kaolin, bentonite, and colloidal silicic acid; and lubricants such as purified talc, stearic acid salts, boric acid powder, and polyethylene glycol. The tablets, if desired, can be coated tablets having a general coat, such as sugar-coated tablets, gelatin-coated tablets, enteric coated tablets, film-coated tablets, double-layered coated tablets, or multilayered coated tablets. In formulating into pills, carriers well known in the art can be used widely. Examples of suitable carriers are excipients such as glucose, lactose, starch, cacao butter, hardened vegetable oils, kaolin, and talc; binders such as gum arabic powder, tragacanth powder, gelatin, and ethanol; and disintegrants such as laminaria and agar. In formulating into suppositories, carriers well known in the art can be used widely. Examples are polyethylene glycol, cacao butter, higher alcohols, higher alcohol asters, gelatin, and semisynthetic glycerides. Capsules are generally prepared by mixing the active ingredient with the above-enumerated various carriers and packing the mixture into hard gelatin capsules or soft capsules. Solutions, emulsions or suspensions as injectable preparations are preferably sterilized and made isotonic with blood. In preparing these preparations, all diluents customarily used in the art, such as water, ethanol, Macrogol, propylene glycol, ethoxylated isostearyl alcohol, polyoxylated isostearyl alcohol, and polyoxyethylene sorbitan fatty acid esters, can be used. Sodium chloride, glucose or glycerol may be incorporated into the injectable preparation in an amount sufficient for making it isotonic. The injectable preparations can contain general dissolution aid, buffers, pain-alleviating agents, and the like. The pharmaceutical compositions can contain coloring agents, preservatives, perfumes, flavors, sweeteners, and other drugs. In formulating the pharmaceutical composition into pastes, creams or gels, a wide variety of diluents known in the art can be used. Examples are white petrolatum, paraffin, glycerol, cellulose derivatives, polyethylene glycol, silicone, and bentonite.

Bases which can be used for an external preparation comprise an oily base or a mixture of two or more oily bases or a water-soluble base or a mixture of two or more water-soluble bases. Examples of suitable bases are fats and oils such as peanut oil, sesame oil, soybean oil, safflower oil, avocado oil, sunflower oil, corn oil, rape seed oil, cotton seed oil, castor oil, camellia oil, palm oil, olive oil, poppy seed oil, coconut oil, beef tallow, lard, and lanolin; modified fats and oils prepared by subjecting the above-described fats and oils to a chemical change such as hydrogenation; mineral oils such as vaseline, paraffin, silicone oil, and squalane; higher fatty acid esters, higher fatty acid alcohols and waxes such as isopropyl myristate, N-butyl myristate, isopropyl linolate, propyl ricinoleate, isopropyl ricinoleate, isobutyl ricinoleate, heptyl ricinoleate, diethyl sebacate, diisopropyl adipate, cetyl alcohol, stearyl alcohol, white beeswax, cetaceum, Japan wax, lanolin, carnauba wax, and shellac wax; higher fatty acids such as stearic acid, oleic acid and palmitic acid; mono-, di- and triglyceride mixtures of saturated or unsaturated fatty acids having 12 to 18 carbon atoms; polyhydric alcohols such as ethylene glycol, polyethylene glycol, propylene glycol, polypropylene glycol, glycerol, butyl alcohol, pentaerythritol, sorbitol, and mannitol; gum such an gum arabic, gum benzoin, guaiac resin, ad gum tragacanth; naturally occurring water-soluble polymers such as gelatin, starch, casein, dextrin, pectin, sodium pectin, sodium alginate, methyl cellulose, ethyl cellulose, carboxyethyl cellulose, hydroxyethyl cellulose, hydroxypropyl cellulose, nitrocellulose, and crystalline cellulose; synthetic water-soluble polymers such as polyvinyl alcohol, polyvinyl methyl ether, polyvinylpyrrolidone, sodium polyacrylate, carboxyvinyl polymers, and polyethyleneimine; nonionic, anionic, amphoteric or cation surfactants; ethanol, isopropyl alcohol, and the like.

These external preparations, if desired, can contain various known bases such as excipients, binders, lubricants, and disintegrants. If desired, they can also contain oily materials such as various fats and oils, waxes, hydrocarbons, fatty acids, higher alcohols, ester oils and metallic soaps, animal or vegetable extracts, pharmaceutically effective components such as vitamins, hormones, and amino acids, surfactants, coloring matters, dyes, pigments, perfumes, antiseptics, antimicrobial agents, humectants, thickeners, antioxidants, sequestering agents, ultraviolet absorbers, ultraviolet scattering agents, or any other known components and additives as long as the effects of the present invention are not impaired.

The amount of the active compound to be incorporated into the rosacea treating agent of the present invention is not particularly limited and can vary over a wide range. A suitable effective amount is usually from about 1 to 70% by weight based on the total composition.

There is no particular restriction on the manner of using the rosacea treating agent, and the treating agent can be administered by routes suitable for the particular forms of the preparation, the age, sex or other conditions of patients, the symptoms, and the like. For example, the tablets, pills, liquid preparations, suspensions, emulsions, granules and capsules are orally administered. The injectable preparations are intravenously administered either alone or together with ordinary auxiliary agents such an glucose and amino acids. As required, the injectable preparations can be singly administered intramuscularly, intracutaneously, subcutaneously or intraperitoneally. The suppositories are administered intrarectally, and the external preparations are applied onto the skin.

The dosage of the rosacea treating agent of the present invention is appropriately selected according to the administration route, the age, sex or other conditions of a patient, the symptoms, etc. Usually, a preferred dose of the active compound is about 0.2 to 100 mg/kg body weight in 3 or 4 divided domes per day. An external preparation is applied once or twice a day at a dose of about 10 mg of the active compound per day.

EXAMPLES

The present invention will now be illustrated in greater detail by way of formulation examples and pharmacological test example.

Formulation Example 1

| | |
|---|---|
| Compound of formula (1) | 200 mg |
| Glucose | 250 mg |
| Injectable distilled water | appropriate amount |
| Total | 5 ml |

The compound of formula (1) and glucose were dissolved in injectable distilled water, and the solution was put into a 5 ml-volume ampule. After substitution with nitrogen, the solution was sterilized by autoclaving at 121° C. for 15 minutes to obtain an injection having the above composition.

Formulation Example 2

| | |
|---|---|
| Compound of formula (1) | 100 g |
| Avicel (trade name, a product of Ashahi Chemical Industry Co., Ltd.) | 40 g |
| Corn starch | 30 g |
| Magnesium stearate | 2 g |
| Hydroxypropylmethyl cellulose | 10 g |
| Polyethylene glycol-6000 | 3 g |
| Castor oil | 40 g |
| Ethanol | 40 g |

The compound of the invention, Avicel, corn starch, and magnesium stearate were mixed, ground, and punched using a pestle of sugar coating R=10 mm. The resulting tablets were coated with a film coating agent comprising hydroxypropyl methyl cellulose, polyethylene glycol-6000, castor oil and ethanol to obtain film-coated tablets.

Formulation Example 3

| | |
|---|---|
| (±)-9-Fluoro-6,7-dihydro-8-(4-hydroxy-1-piperidyl)-5-methyl-1-oxo-1H, 5H-benzo[i, j]quinolizine-2-carboxylic acid | 2 g |
| Purified lanolin | 5 g |
| White Beeswax | 5 g |
| White petrolatum | 88 g |
| Total | 100 g |

White beeswax was liquefied by heating, and the compound of the invention, purified lanolin and white petrolatum were added thereto. After once heated to liquefy, the mixture was stirred till it began to solidify to obtain an ointment of the above composition.

Formulation Example 4

| Cream: | |
|---|---|
| (±)-9-Fluoro-6,7-dihydro-8-(4-hydroxy-1-piperidyl)-5-methyl-1-oxo-1H, 5H-benzo[i, j]quinolizine-2-carboxylic acid | 1.0 g |
| White petrolatum | 10.0 g |
| Light liquid paraffin | 9.0 g |
| Stearyl alcohol | 4.0 g |
| Polyoxyethylene cetyl ether | 3.0 g |
| Concentrated glycerin | 10.0 g |
| Purified water and the like | appropriate amount |
| Total | 100.0 g |

Formulation Example 5

| Component I: | |
|---|---|
| White petrolatum | 10.0 g |
| Light liquid paraffin | 9.0 g |
| Stearyl alcohol | 4.0 g |
| Cetanol | 4.0 g |
| Polyoxyethylene cetyl ether | 3.0 g |
| Component II: | |
| (±)-9-Fluoro-6,7-dihydro-8-(4-hydroxy-1-piperidyl)-5-methyl-1-oxo-1H, 5H-benzo[i, j]quinolizine-2-carboxylic acid | 1.0 g |
| Glycerin | 10.0 g |
| Di(β-hydroxyethyl)amine | 0.1 g |
| Purified water | 58.9 g |

An external preparation in cream form was obtained in the same manner as in Formulation Example 4.

Formulation Example 6

| Ointment: | |
|---|---|
| White petrolatum | 73.54 g |
| Light liquid paraffin | 10.0 g |
| Cetanol | 5.0 g |
| Cholesterol | 4.0 g |
| (±)-9-Fluoro-6,7-dihydro-8-(4-hydroxy-1-piperidyl)-5-methyl-1-oxo-1H, 5H-benzo[i, j]quinolizine-2-carboxylic acid | 1.0 g |
| Sodium hydroxide | 0.112 g |
| Propylene glycol | 5.0 g |
| Di(β-hydroxyethyl)amine | 0.2 g |
| Disodium edetate | 0.1 g |
| Purified water | 1.048 g |

Formulation Example 7

| Component I: | |
|---|---|
| White petrolatum | 6.5 g |
| Light liquid paraffin | 6.0 g |
| Stearyl alcohol | 2.5 g |

-continued

| | |
|---|---|
| Cetanol | 2.5 g |
| Polyoxyethylene cetyl ether | 2.0 g |
| Component II: | |
| (±)-9-Fluoro-6,7-dihydro-8-(4-hydroxy-1-piperidyl)-5-methyl-1-oxo-1H, 5H-benzo[i, j]quinolizine-2-carboxylic acid | 1.0 g |
| Sodium hydroxide | 0.112 g |
| Di(β-hydroxyethyl)amine | 0.36 g |
| Purified water | 79.028 g |

Component I was heated to about 80° C. to melt. Separately, component II was mixed, dissolved, and heated to about 80° C. The heated components I and II were mixed and cooled to obtain an external preparation in emulsion form.

Formulation Example 8

| | |
|---|---|
| Lotion: | |
| (±)-9-Fluoro-6,7-dihydro-8-(4-hydroxy-1-piperidyl)-5-methyl-1-oxo-1H, 5H-benzo[i, j]quinolizine-2-carboxylic acid | 1.0 g |
| Isopropyl alcohol | 62.4 g |
| Propylene glycol | 2.5 g |
| Tri(β-hydroxyethyl)amine | 0.4 g |
| Sodium hydroxide | 0.2 g |
| Purified water | appropriate amount |
| Total | 1000 ml |

Test Example

A cream prepared in accordance with Formulation Example 4, which contained 1% of (±)-9-fluoro-6,7-dihydro-8-(4-hydroxy-1-piperidyl)-5-methyl-1-oxo-1H, 5H-benzo[i,j]-quinolizine-2-carboxylic acid, was applied to the face of 13 rosacea patients suffering from facial flush and 15 or more active pustules or papules on their face twice a day. Of the 13 cases, 11 had received medical treatment with minocycline (6 cases), metronidazole (5 cases), oxytetracycline (2 cases), erythromycin (2 cases), tetracycline (1 case), benzoyl peroxide (1 case), zinc acetate (1 case), doxycycline (1 case), fluocinonide (1 case), nystatin (1 case) or white petrolatum (1 case).

After 12 weeks from the start of the treatment with the cream, the physician in charge judged the degree of overall improvement in the patients on cream therapy based on 5 scales of cure, remarkable improvement, improvement, no change, and aggravation. As a result, of 13 cases 2 cases (15.4% of the total) were judged as cure and 9 cases (69.2% of the total) as remarkable improvement, proving that the rate of improvement reached 84.6%. There were only 2 cases (15.4% of the total) judged as no change.

It is seen from these results that the rosacea treating agent according to the present invention brings about improvement on rosacea symptoms, exhibiting effectiveness even on those patients who had not been cured completely by previous therapy.

INDUSTRIAL APPLICABILITY

The benzoheterocyclic derivatives of formula (1) and salts thereof are useful as a rosacea treating agent that is effective even on baffling and intractable rosacea which cannot be cured completely by conventional antibiotics such an minocycline, has low toxicity, causes little side effect, and is of long duration.

What is claimed is:

1. A rosacea treating agent comprising, as an active ingredient, at least one selected from the group consisting of benzoheterocyclic derivatives represented by the following formula (1):

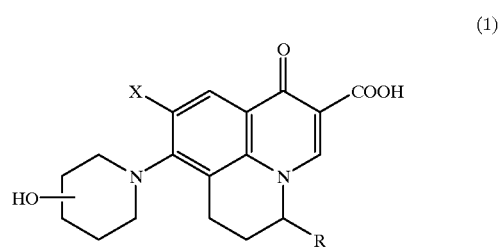

(1)

wherein R represents a lower alkyl group; and X represents a halogen atom, and salts thereof.

2. The rosacea treating agent according to claim 1, wherein the active ingredient is at least one selected from the group consisting of (±)-9-fluoro-6,7-dihydro-8-(4-hydroxy-1-piperidyl)-5-methyl-1-oxo-1H, 5H-benzo[i,j]-quinolizine-2-carboxylic acid and salts thereof.

3. A method for preparing a rosacea treating agent by compounding the rosacea treating agent into a pharmaceutical composition together with one or more common pharmaceutically acceptable carriers, wherein said rosacea treating agent comprises at least one compound selected from the group consisting of benzoheterocyclic derivatives represented by formula (1) according to claim 1 and salts thereof.

4. A method for treating rosacea by administering a dosage form of a pharmaceutical composition to a rosacea patient;

wherein, said pharmaceutical composition comprises a rosacea treating agent and one or more common pharmaceutically acceptable carriers, and said rosacea treating agent comprises at least one compound selected from the group consisting of benzoheterocyclic derivatives represented by formula (1) according to claim 1 and salts thereof.

5. The method for treating rosacea of claim 4, wherein said benzoheterocyclic derivatives is at least one selected from the group consisting of (±)-9-fluoro-6,7-dihydro-8-(4-hydroxy-1-piperidyl)-5-methyl-1-oxo-1H, 5H-benzo [i,j]-quinolizine-2-carboxylic acid and salts thereof.

* * * * *